US011471274B2

(12) United States Patent
Whitsett

(10) Patent No.: US 11,471,274 B2
(45) Date of Patent: Oct. 18, 2022

(54) TORIC LENS GUIDE FOR USE IN CONJUNCTION WITH A TORIC INTRAOCULAR LENS SO AS TO PROPERLY ORIENT THE TORIC LENS IN ORDER TO PROPERLY CORRECT ASTIGMATISM

(71) Applicant: Jeffrey Whitsett, Houston, TX (US)

(72) Inventor: Jeffrey Whitsett, Houston, TX (US)

( * ) Notice: Subject to any disclaimer, the term of this patent is extended or adjusted under 35 U.S.C. 154(b) by 402 days.

(21) Appl. No.: 16/812,320

(22) Filed: Mar. 8, 2020

(65) Prior Publication Data

US 2021/0038371 A1 Feb. 11, 2021

Related U.S. Application Data

(60) Provisional application No. 62/883,817, filed on Aug. 7, 2019.

(51) Int. Cl.
*A61F 2/16* (2006.01)
(52) U.S. Cl.
CPC .......... *A61F 2/1662* (2013.01); *A61F 2/1645* (2015.04); *A61F 2002/1681* (2013.01); *A61F 2002/16903* (2015.04); *A61F 2250/0096* (2013.01); *A61F 2250/0097* (2013.01)
(58) Field of Classification Search
CPC .................. A61F 2/1645; A61F 2/1662; A61F 2002/16903
See application file for complete search history.

(56) References Cited

U.S. PATENT DOCUMENTS

| 6,419,697 | B1* | 7/2002 | Kelman | A61F 2/1602 623/6.43 |
| 9,387,069 | B2* | 7/2016 | Kahook | A61F 2/1664 |
| 9,421,089 | B2* | 8/2016 | Zadno-Azizi | A61F 2/1613 |
| 2004/0015235 | A1* | 1/2004 | Worst | A61F 2/1662 623/6.46 |
| 2007/0270947 | A1* | 11/2007 | Peyman | A61F 2/1648 623/6.34 |
| 2011/0307058 | A1* | 12/2011 | Beer | A61F 2/1629 623/6.43 |
| 2014/0200666 | A1* | 7/2014 | Phillips | A61F 9/00827 623/6.46 |
| 2018/0085256 | A1* | 3/2018 | Gray | A61F 2/1613 |

* cited by examiner

*Primary Examiner* — Javier G Blanco
(74) *Attorney, Agent, or Firm* — Law Offices of Steven W. Weinrieb

(57) ABSTRACT

A toric lens guide comprises a substantially linear bar member and a pair of crab claw members fixedly attached to opposite ends of the linear bar member. The toric lens guide is adapted to be mounted upon an intraocular lens (IOL) which has been implanted within the capsular bag of a human eye during cataract surgery such that the substantially linear bar member is adapted to be disposed atop the central optic component of the intraocular lens (IOL) while the crab claw members effectively grasp the optica/haptic junctions of the intraocular lens (IOL). After the intraocular lens (IOL) is implanted within the capsular bag, it is rotated within the capsular bag such that the substantially linear bar member of the toric lens guide will effectively define a diametrical vector across the intraocular lens (IOL) such that the cataract surgeon can precisely orient the intraocular lens (IOL) within the capsular bag such that the patient's astigmatism is optimally corrected.

7 Claims, 4 Drawing Sheets

TORIC LENS GUIDE FOR USE IN CONJUNCTION WITH A TORIC INTRAOCULAR LENS SO AS TO PROPERLY ORIENT THE TORIC LENS IN ORDER TO PROPERLY CORRECT ASTIGMATISM

CROSS-REFERENCE TO RELATED PATENT APPLICATION

This United States Non-Provisional Patent Application Is A Non-Provisional Perfection of United States Provisional Patent Application, Application No. 62/883,817 which was filed on Aug. 7, 2019, the priority benefits of which are hereby claimed.

FIELD OF THE INVENTION

The present invention relates generally to medical equipment, and more particularly to a toric lens guide which is utilized in conjunction with a toric intraocular lens (IOL) during cataract surgery so as to effectively assist the surgeon in properly orienting the toric intraocular lens (IOL) within the capsular bag such that the implanted toric intraocular lens (IOL) will in fact properly correct the patient's astigmatism. More specifically, a toric intraocular lens (IOL) comprises a central optic component and a pair of curved haptic components which extend outwardly from diametrically opposite locations, along the circumferential periphery of the central optic component, so as to effectively extend in opposite directions and to define with the central optic component of the toric intraocular lens, haptic/optic junctions. The haptic components effectively define flexible arms such that when the toric intraocular lens is inserted into the capsular bag, the haptic components will be forced radially inwardly toward the axis of the toric intraocular lens (IOL) such that the haptic components always engage the internal wall portion of the capsular bag with a predetermined amount of biasing force. As can therefore be appreciated, when the surgeon performing the cataract surgery implants the tonic intraocular lens within the capsular bag and rotates the toric intraocular lens (IOL) to a predetermined vector orientation with respect to the cornea of the eye, the haptic components will permit such proper rotation of the toric intraocular lens (IOL), relative to the cornea of the eye, to occur, however, upon completion of the final rotation of the toric intraocular lens (IOL) to the predetermined axial position relative to the cornea of the eye, the haptic components will then also serve to maintain the orientation of the toric intraocular lens (IOL) at the set rotational angle of the toric intraocular lens (IOL) relative to the cornea of the eye as a result of frictional bias developed between the distal end portions of the haptic arms and the internal peripheral wall of the capsular bag. It is also critical that this rotational angle of the toric intraocular lens (IOL) relative to the cornea of the eye be precise so as to in fact permit the toric intraocular lens (IOL) to achieve the desired correction of the patient's astigmatism. The toric lens guide of the present invention has therefore been developed so as to in fact achieve this specific goal.

BACKGROUND OF THE INVENTION

With modern advancements in cataract surgery techniques and procedures, toric intraocular lenses (IOLs) can now be implanted within a patient's eye so as to correct various deficiencies in a patient's eye, such as, for example, myopia, hyperopia, and astigmatism, which may occur as a patient ages. Astigmatism is a common occurrence in patients wherein, in lieu of the cornea, for example, being perfectly round, the cornea becomes elongated wherein, in effect, the cornea is somewhat elliptical whereby one axis is longer than the other. In order to correct this curvature, a toric introcular lens (IOL) is utilized. More particularly, after the patient's original lens has been removed during cataract surgery, usually by well-known phacoemulsification techniques, the toric intraocular lens (IOL) is inserted into the capsular bag and rotated to a particular vector orientation relative to the capsular bag, as well as with respect to the cornea, such that the adverse effects of the astigmatism can be neutralized. However, it is sometimes difficult for the surgeon to know if the toric intraocular lens (IOL) has in fact been rotated within the capsular bag to the proper or precise degree of orientation such that the adverse effects of the astigmatism can in fact be neutralized.

A need therefore exists in the art for a new device or implement which will assist the cataract surgeon during cataract surgery. Another need exists in the art for a new device or implement which will assist the cataract surgeon during cataract surgery such that the adverse effects of astigmatism can in fact be minimized. Still another need exists in the art for a new device or implement which will assist the cataract surgeon during cataract surgery as a result of the cataract surgeon implanting a tonic intraocular lens (IOL) with the capsular bag of the eye such that the adverse effects of astigmatism can in fact be minimized. Yet another need exists in the art for a new device or implement which will assist the cataract surgeon during cataract surgery as a result of the cataract surgeon implanting a toric intraocular lens (IOL) within the capsular bag of the eye and wherein the toric intraocular lens (IOL) will be properly oriented within the capsular bag with respect to the capsular bag and the cornea such that the adverse effects of astigmatism can in fact be minimized. Yet still another need exists in the art for a new device or implement which will assist the cataract surgeon during cataract surgery as a result of the cataract surgeon implanting a tonic intraocular lens (IOL) within the capsular bag and wherein the new device or implement will operatively cooperate with the tonic intraocular lens (IOL) so as to ensure that the toric intraocular lens (IOL) will in fact be properly oriented within the capsular bag with respect to the capsular bag and the cornea such that the adverse effects of astigmatism can in fact be minimized.

Overall Objectives of the Present Invention

An overall objective of the present invention is to provide a novel device or implement which will assist the cataract surgeon during cataract surgery. Another overall objective of the present invention is to provide a novel device or implement which will assist the cataract surgeon during cataract surgery such that the adverse effects of astigmatism can in fact be minimized. Still another overall objective of the present invention is to provide a novel device or implement which will assist the cataract surgeon during cataract surgery as a result of the cataract surgeon implanting a toric intraocular lens (IOL) with the capsular bag of the eye such that the adverse effects of astigmatism can in fact be minimized. Yet another overall objective of the present invention is to provide a novel device or implement which will assist the cataract surgeon during cataract surgery as a result of the cataract surgeon implanting a toric intraocular lens (IOL) within the capsular bag of the eye and wherein the toric intraocular lens (IOL) will be properly oriented within the capsular bag with respect to the capsular bag and the cornea such that the adverse effects of astigmatism can in fact be minimized. Yet still another overall objective of the present invention is to provide a novel device or implement which will assist the cataract surgeon during cataract surgery as a result of the cataract surgeon implanting a toric intraocular lens (IOL) within the capsular bag and wherein the new device or implement will operatively cooperate with the toric intraocular lens (IOL) so as to ensure that the toric intraocular lens (IOL) will in fact be properly oriented within the capsular bag with respect to the capsular bag and the cornea such that the adverse effects of astigmatism can in fact be minimized.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein.

DETAILED DESCRIPTION OF THE PRESENT INVENTION

Figure 1:
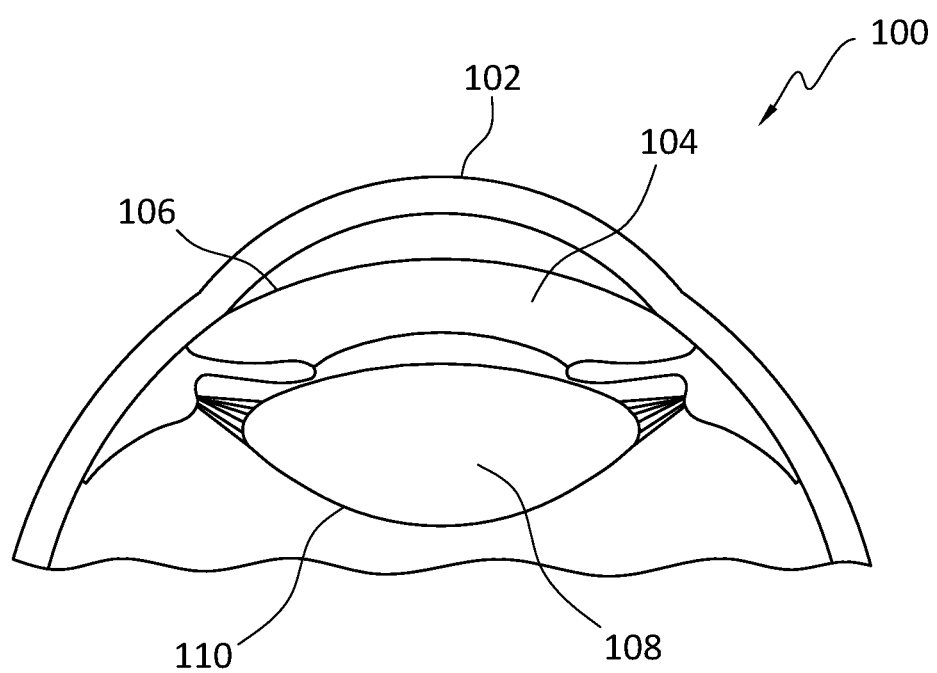
FIG. 1 is a cross-section of a human eye disclosing the various components of the human eye.

With reference being firstly made to FIG. 1, a cross-section of a human eye is illustrated for background purposes and is generally indicated by the reference character 100. As is illustrated, it is seen that the human eye 100 comprises, among other components, the cornea 102, the iris 104, the pupil 106, and the lens 108 disposed within the capsular bag 110.

As a result of cataract surgery, as has been described briefly hereinbefore, the lens 108 will be removed and a toric intraocular lens (IOL) 112 will effectively be substituted for the lens 108 when inserted into the capsular bag 110 by means of the cataract surgeon performing the cataract surgery. The disposition of the toric intraocular lens (IOL) 112 within the capsular bag 110 is illustrated within FIG. 2.

Figure 2:
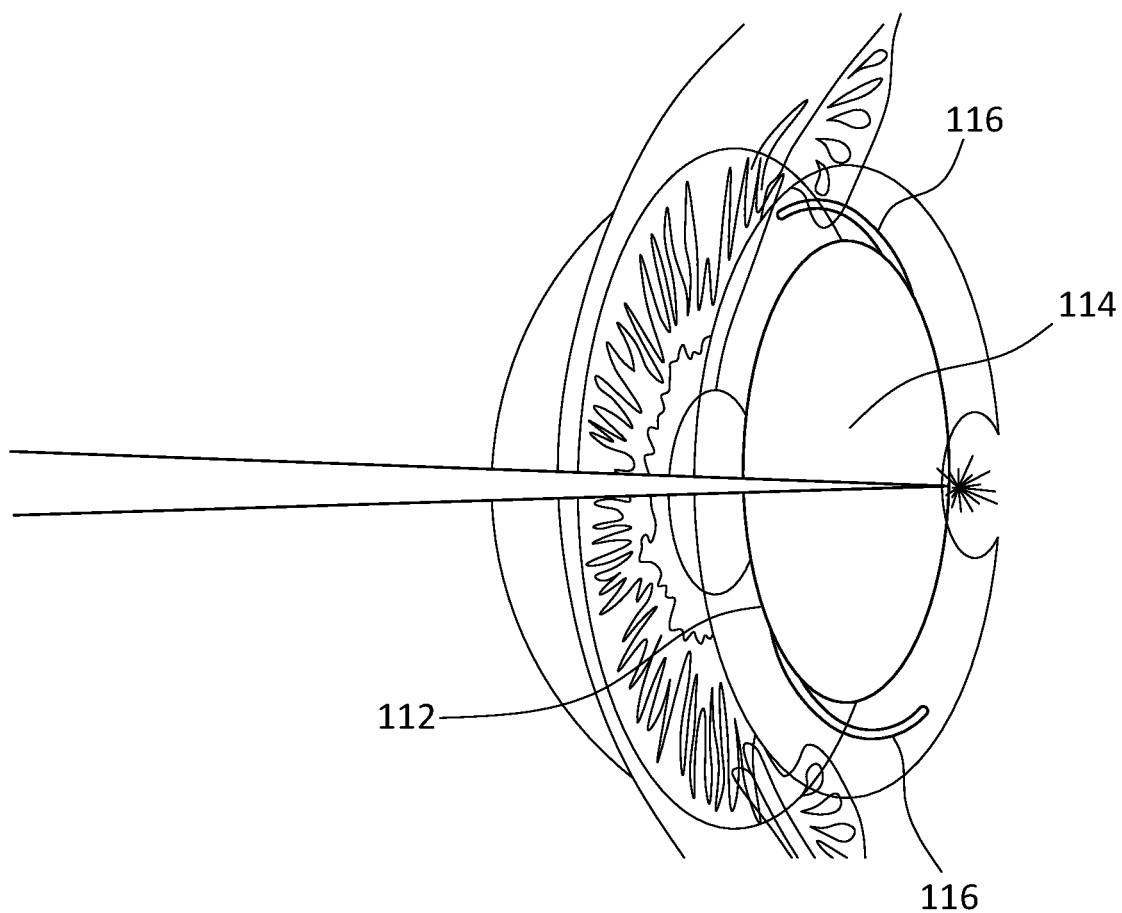
FIG. 2 is a cross-section of a human eye having an intraocular lens (IOL) inserted into the capsular bag.
Figure 3:
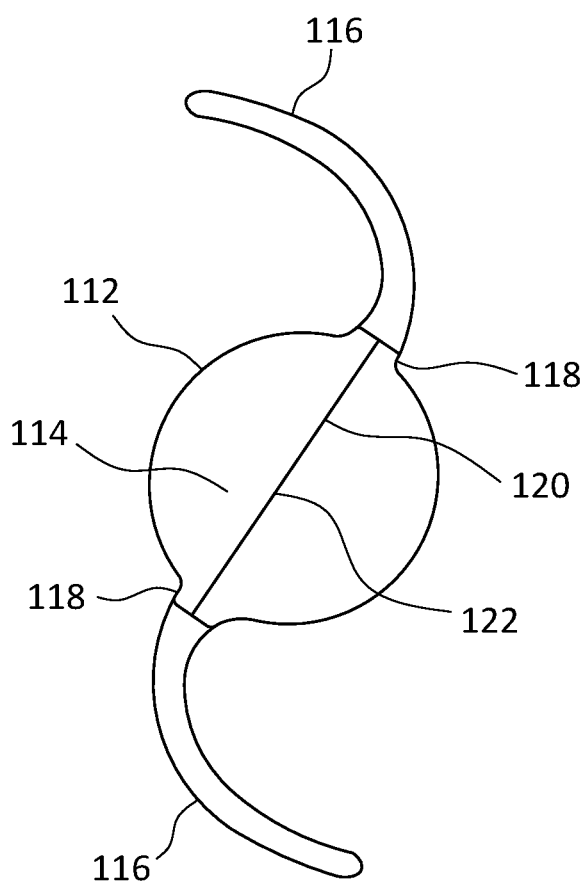
FIG. 3 is a plan view of a toric intraocular lens (IOL) having the toric lens guide of the present invention mounted thereon at the haptic/optic junctions.

As can be appreciated from FIG. 2, as well as FIG. 3, the toric intraocular lens (IOL) 112 comprises a central optic component 114 and a pair of curved haptic components 116,116 which extend outwardly from diametrically opposite locations, along the circumferential periphery of the central optic component 114, so as to effectively extend in opposite directions and to define with the central optic component 114 of the toric intraocular lens 112, haptic/optic junctions 118,118. The haptic components 116,116 effectively define flexible arms such that when the toric intraocular lens 112 is inserted into the capsular bag 110, the haptic components 116,116 will be forced radially inwardly toward the axis of the toric intraocular lens (IOL) 112 such that the haptic components always engage the internal wall portion of the capsular bag 110 with a predetermined amount of biasing force. As can therefore be appreciated, when the cataract surgeon performing the cataract surgery implants the toric intraocular lens 112 within the capsular bag 110, and rotates the toric intraocular lens (IOL) 112 to a predetermined vector orientation with respect to the cornea 102 of the eye 100, the haptic components 116,116 will permit such proper rotation of the toric intraocular lens (IOL) 112, relative to the cornea 102 of the eye 100 and the capsular bag 110 of the eye 100, to occur, and, upon completion of the final rotation of the toric intraocular lens (IOL) 112 to the predetermined axial position relative to the cornea 102 of the eye 100 and the capsular bag 110 of the eye 100, the haptic components 116, 116 will then serve to maintain the orientation of the toric intraocular lens (IOL) 112 at the pre-set rotational angle of the toric intraocular lens (IOL) 112 relative to the cornea 102 of the eye 100 and the capsular bag 110 of the eye 100 as a result of frictional bias developed between the distal end portions of the haptic arms 116,116 and the internal peripheral wall of the capsular bag 110.

As has been noted, however, it is sometimes difficult, particularly in those patients which relatively small pupils, for the cataract surgeon performing the cataract surgery to know if the toric intraocular lens (IOL) 112 has in fact been correctly rotated within the capsular bag 110 to the proper orientation such that the adverse effects of astigmatism can in fact be neutralized.

Figure 4:
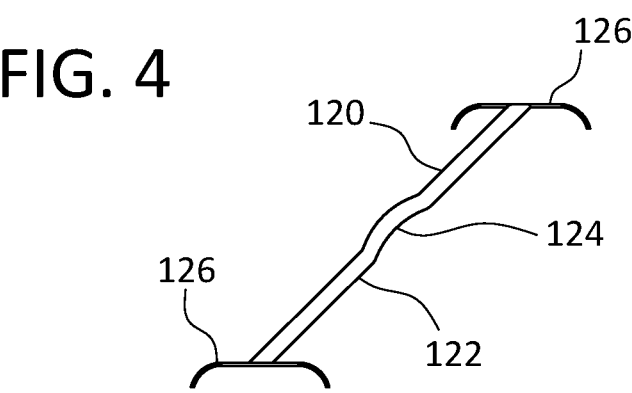
FIG. 4 is a perspective view of the toric lens guide of the present invention.
Figure 5:
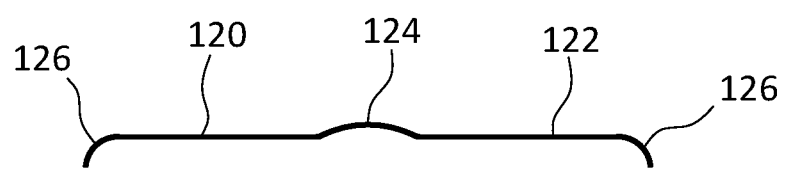
FIG. 5 is a cross-sectional view of the toric lens guide as illustrated within FIGS. 3 and 4.
Figure 3A:
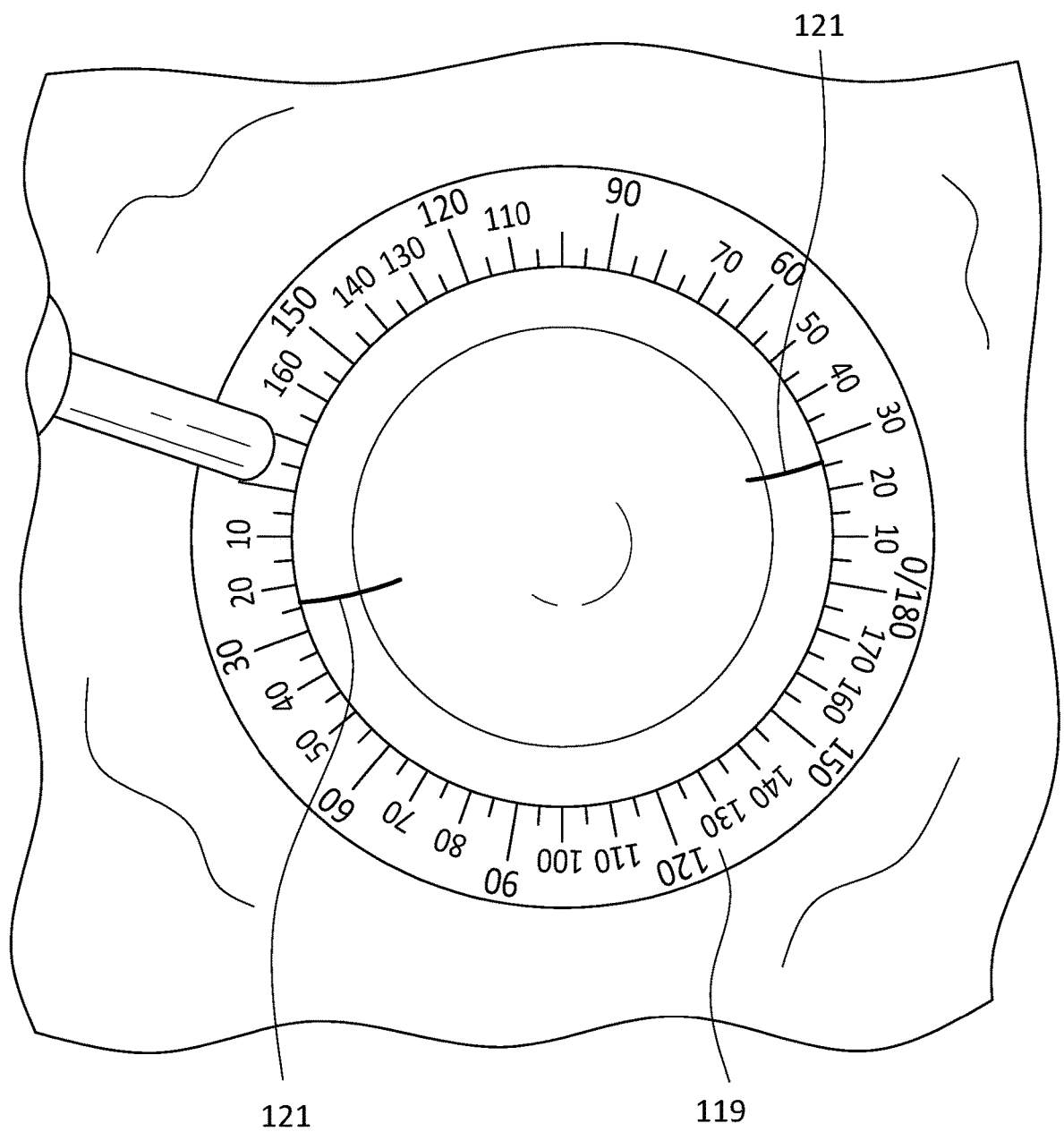
FIG. 3a is a view showing how a cataract surgeon employs a Mendez marker so as to apply diametrically opposed marks upon the patient's cornea so as to indicate the plane within which the toric lens guide is to be disposed and thereby properly orient the toric intraocular lens (IOL) within the capsular bag.

Therefore, in accordance with the principles and teachings of the present invention, there has been developed a toric lens guide 120 which is illustrated within FIGS. 4 and 5, and which is also illustrated as being operatively attached to the toric intraocular lens (IOL) 112 in FIG. 3. More particularly, the cataract surgeon will employ a Mendez marker 119 so as to permit the cataract surgeon to actually mark diametrically opposite portions of the cornea which represent the axis along which the astigmatism extends, as indicated at 121,121 within FIG. 3a. It is seen that the toric lens guide 120 comprises an elongated substantially linear bar member 122 having a central hinge section 124 and a pair of arcuate crab claws 126,126 at its opposite ends. As can be best appreciated from FIG. 3, the toric lens guide 120 is adapted to be mounted upon the toric intraocular lens (IOL) 112 such that the arcuate crab claws 126,126 of the toric lens guide 120 are seated upon the diametrically oppositely disposed haptic/optic junctions 118,118. In this manner, it can be further appreciated, as clearly illustrated within FIG. 3, that the elongated linear bar member 122 effectively defines a vector axis which extends diametrically across the optic component 114 of the toric intraocular lens (IOL) 112, wherein such vector is predeterminedly aligned with the diametrically extending axis of the toric intraocular lens (IOL) 112 which, when correctly rotated and positioned within the eye so as to extend between the marks noted upon the cornea, will achieve the desired correction of the patient's astigmatism. In this manner, the surgeon is clearly enabled to properly rotate the toric intraocular lens (IOL) 112 to its proper orientation within the capsular bag 110 of the eye 100 once the toric intraocular lens (IOL) 112 is inserted within the capsular bag 110. Subsequently, once the toric intraocular lens (IOL) 112 has been rotated to its optimum vector orientation within the capsular bag 110, the toric lens guide 120 may be easily removed as a result of the same being capable of folding itself in half at the central hinge section 124.

Obviously, many variations and modifications of the present invention are possible in light of the above teachings. It is therefore to be understood that within the scope of the appended claims, the present invention may be practiced otherwise than as specifically described herein.

REFERENCE NUMBER GUIDE

100—Human eye
102—Cornea of eye
104—Iris of eye
106—Pupil of eye
108—Lens of eye
110—Capsular bag of eye
112—Intraocular lens (IOL)
114—Central optical component of IOL
116—Haptic ends of IOL
118—Optic/haptic junctions of IOL
119—Mendez Marker
120—Toric lens guide
121—Marks marked upon patient's cornea
122—Linear bar member of 120
124—Central hinge portion of 120
126—Crab claw ends of 120

What is claimed and desired to be protected by Letters Patent is:

1. A toric lens guide, for use with a toric intraocular lens (IOL) comprising a central optic component and a pair of diametrically opposite haptic components connected to the central optic component by diametrically opposite haptic/optic junctions, for correcting astigmatism when the toric intraocular lens (IOL) is implanted within a capsular bag of an eye during cataract surgery, comprising:
an elongated substantially linear bar member sized and configured to be mounted upon the central optic component of the toric intraocular lens (IOL); and
wherein said elongated substantially linear bar member of said toric lens guide comprises opposite ends which are to be attached to the pair of diametrically opposite haptic/optic junctions of the toric intraocular lens (IOL) so as to enable a cataract surgeon, performing the cataract surgery, to properly rotate the toric intraocular lens (IOL) within the capsular bag of the eye whereby, as the intraocular lens (IOL) is rotated within the capsular bag of the eye, said elongated substantially linear bar member will effectively define a vector extending diametrically across the central optic component of the toric intraocular lens (IOL) so as to achieve the best correction of the astigmatism.

2. The toric lens guide as set forth in claim 1, wherein:
a pair of crab claws are fixedly secured to said opposite ends of said elongated substantially linear bar member for enabling said elongated substantially linear bar member to be mounted upon the central optic component of the toric intraocular lens (IOL) as a result of said pair of crab claws, mounted upon said opposite ends of said elongated substantially linear bar member, grasping the pair of diametrically opposite haptic/optic junctions of the intraocular lens (IOL).

3. The toric lens guide as set forth in claim 1, wherein:
said elongated substantially linear bar member has a central hinge portion so as to facilitate removal of said toric lens guide from the intraocular lens (IOL) once the toric intraocular lens (IOL) has been angularly rotated to its proper vector orientation within the capsular bag of the eye.

4. A method for effectively correcting astigmatism, as best as possible, within a human eye that has had a toric intraocular lens (IOL) implanted within the eye, wherein the toric intraocular lens (IOL) comprises a central optic component and a pair of diametrically opposite haptic components connected to the central optic component by diametrically opposite haptic/optic junctions, comprising the step of:
mounting a toric lens guide, comprising an elongated substantially linear bar member, upon the central optic component of the toric intraocular lens (IOL) such that said elongated substantially linear bar member is attached to the pair of diametrically opposite haptic/optic junctions of the toric intraocular lens (IOL) so as to enable a cataract surgeon, performing the cataract surgery, to properly rotate the toric intraocular lens (IOL) within the capsular bag of the eye whereby, as the intraocular lens (IOL) is rotated within the capsular bag of the eye, said elongated substantially linear bar member will effectively define a vector extending diametrically across the central optic component of the toric intraocular lens (IOL) so as to achieve the best correction of the astigmatism.

5. The method as set forth in claim 4, further comprising the step of:
fixedly securing a pair of crab claws to opposite ends of said elongated substantially linear bar member for enabling said elongated substantially linear bar member to be mounted upon the central optic component of the toric intraocular lens (IOL) as a result of said pair of crab claws being mounted upon and grasping the pair of diametrically opposite haptic/optic junctions of the intraocular lens (IOL).

6. The method as set forth in claim 4, further comprising the step of:
using a Mendez marker to mark diametrically opposite locations upon the patient's cornea such that the cataract surgeon can easily align said elongated substantially linear bar member of said toric lens guide with the diametrically opposite locations upon the patient's cornea whereby said elongated substantially linear bar member of said toric lens guide will in fact provide the cataract surgeon with the proper vector such that the cataract surgeon is assured that the intraocular lens (IOL) has in fact been properly rotated to the proper orientation relative to the capsular bag so as to achieve the best correction of the astigmatism.

7. The method as set forth in claim 4, further comprising the step of:
providing said elongated substantially linear bar member with a central hinge portion so as to facilitate removal of said toric lens guide from the intraocular lens (IOL) once the toric intraocular lens (IOL) has been angularly rotated to its proper vector orientation within the capsular bag of the eye.

* * * * *